ELECTRONIC STANDBY DEFIBRILLATOR

Original Filed Feb. 9, 1970 2 Sheets-Sheet 1

INVENTORS
MIECZYSLAW MIROWSKI
MORTON M. MOWER
WILLIAM S. STAEWEN
BY Fulbright, Gipple & Jacobson
ATTORNEYS

ELECTRONIC STANDBY DEFIBRILLATOR

Original Filed Feb. 9, 1970 2 Sheets-Sheet 2

INVENTORS
MIECZYSLAW MIROWSKI
MORTON M. MOWER
WILLIAM S. STAEWEN
BY Fleit, Gipple & Jacobson
ATTORNEYS United States Patent Office Re. 27,652
Reissued May 29, 1973

27,652

ELECTRONIC STANDBY DEFIBRILLATOR

Mieczyslaw Mirowski, Owings Mills, Morton M. Mower, Baltimore, and William S. Staewen, Belair, Md., assignors to Mieczyslaw Mirowski, Owings Mills, Md.

Original No. 3,614,954, dated Oct. 26, 1971, Ser. No. 9,934, Feb. 9, 1970. Application for reissue Feb. 25, 1972, Ser. No. 229,593

Int. Cl. A61n *1/36*

U.S. Cl. 128—419 D 13 Claims

Matter enclosed in heavy brackets [ ] appears in the original patent but forms no part of this reissue specification; matter printed in italics indicates the additions made by reissue.

ABSTRACT OF THE DISCLOSURE

A method and means for automatically defibrillating a malfunctioning heart. With the present invention, the heart function is continuously monitored. When the function becomes abnormal, the malfunctioning heart is automatically shocked by a voltage of substantial size. If the heart does not return to its normal functions after a given interval, then it is again shocked. Normal heart activity ensures that the shocking mechanism remains inert.

BACKGROUND OF THE INVENTION

During the past several decades, coronary heart disease has come to occupy the first position among the causes of death in the developed areas of the world. In the United States, for example, this disease is responsible for over one-half million deaths yearly. And of this number, more than half occur suddenly outside the hospital, and therefore before the patient is able to obtain the necessary medical assistance. Although the precise cause of sudden death in coronary heart disease has not yet been entirely clarified, the available evidence permits the medical field to ascribe death in the majority of these cases to grave disturbances in cardiac electrical activity resulting in ventricular fibrillation.

Recent experience has clearly demonstrated that ventricular fibrillation and its frequent precursor, ventricular tachycardia, are reversible phenomena when prompt defibrillation of the heart is instituted. Under such circumstances, cardiac function can frequently be restored to normal without the patient suffering from residual disability. Unfortunately, however, the state of the art makes defibrillation very much dependent upon a highly specialized medical environment, thus limiting such treatment to elaborately equipped modern hospitals.

At the present, therefore, a great need exists for a defibrillator which could be carried by those who are prone to having one of the many life threatening arrhythmias generally discussed above. Thus, in some patients having coronary heart diseases, a fatal outcome from ventricular tachycardia or ventricular fibrillation could be avoided, even in the absence of immediate medical assistance. The first step, of course, is the detection of those prone to suffering from cardiac malfunctions leading to ventricular tachycardia or ventricular fibrillation.

While it is not possible to predict with unerring exactness which patient suffering from coronary heart disease will be the victim of sudden death, several high risk groups of patients can be recognized. For example, patients who have experienced myocardia infarction, even though they may be surviving in good health, run a substantial risk of dying suddenly, a risk several times greater than that associated with the general population. Further, if patients with myocardial infarction have a history of serious ventricular arrhythmias and/or of cardiac arrest, or if evidence of persistent myocardial irritability is present, it may be logically assumed that the risk of sudden death is increased substantially. Patients like those described above would greatly benefit if an automatic, standby or demand defibrillator were available.

Also, such an automatic defibrillator would be an asset to those hospital patients who have suffered myocardial infarction and who have been discharged from the well-equipped coronary care unit. Under such circumstances, the defibrillator could be implanted temporarily for the remainder of the expected hospital stay; or the defibrillator could be permanently implanted for use both in the hospital and after discharge. And another recognizable class of patients particularly in need of any automatic defibrillator is the class composed of those who have not shown prior histories of myocardia infarction but who show severe symptoms of coronary heart disease, such as ventricular arrhythmias resistant to medical treatment or angina pectoris.

From the brief discussion above, there should be little doubt that the possible applications for an automatic defibrillator are numerous. And, as previously noted, there is at present no known device which meets the need. It is toward filling this gap in medical instrumentation that the present invention is directed.

SUMMARY OF THE INVENTION

The present invention relates to a standby defibrillator, an electronic system which, after detecting one of the above-noted life threatening arrhythmias, automatically defibrillates the heart of the user. The system of the present invention may be installed in patients particularly prone to develop ventricular tachyacadia and/or ventricular fibrillation, either on a temporary or a permanent basis. And, because of its small size, the device of the present invention may be entirely implanted under the skin of the patient, or alternatively, may be carried externally, save for the sensing electrode and one shock-applying electrode.

More particularly, the present invention relates to a device for reliably sensing the differences between a properly functioning heart and one which has suddenly developed ventricular fibrillation, and which then delivers a defibrillating shock to the heart in fibrillation. The device is adapted to continue delivering intermittent shocks to the heart in the event that the heart fails to return to its normal behavior pattern, and has the ability of automatically regaining sensing control over a functional heart thereby ensuring that further shocks are inhibited after successful defibrillation has taken place.

The standby defibrillator of the present invention has as its basic element, a capacitor capable of storing electrical energy in an amount sufficient to depolarize the human heart (on the order of 50 joules). Upon discharge of this capacitor, a shock is delivered to the heart through two stimulating electrodes. One of these electrodes is positioned within the right ventricle, thereby forming the distal tip of an intracardia catheter. This electrode is introduced through a peripheral vein. The second stimulating electrode is positioned either on the surface of the chest, or is sutured under the skin of the anterior chest wall or directly to the ventricular myocardium.

The capacitor is associated with a sensing circuit connected to the proximal end of the intracardiac catheter and is adapted to respond to a signal recorded at the distal end of the catheter. The signal sensed by the catheter must, of course, be inherently related to some distinctive characteristic of ventricular tachycardia or ventricular fibrillation; and in a specific embodiment of the present invention, the pressure in the right ventricle is sensed. When this pressure falls below a given value, on the order of 10 to 15 mm. Hg, the heart is malfunctioning and, therefore, the capacitor is discharged into the heart.

Between the sensing circuit and the capacitor, means are provided for delaying the repetition of depolarizing discharges for a preset period of time (on the order of 20 to 30 seconds). This delay is essential to give the heart the opportunity to convert spontaneously to a normal cardiac rhythm, and also to ensure that the abnormal heart conditions are, in fact, critical. Only in the absence of a successful conversion is a subsequent shock delivered to the heart. In a particular embodiment of the present invention, the time delay is brought about with the air of a sawtooth generator, a relay and the charge time of the storage capacitor.

Accordingly, it is the main object of the present invention to provide a compact and automatic standby defibrillator which lies dormant during normal heart activity but which applies a shock to the heart when the heart functions become abnormal.

It is another object of the present invention to provide a standby defibrillator which reliably senses the difference between a normally functioning heart and one that has suddenly developed abnormal function, and which then automatically delivers a defibrillating shock to the heart.

It is a further object of the present invention to provide a standby defibrillator which is capable of delivering multiple shocks in the event that the heart is not successfully cardioverted by the initial shock.

It is yet a further object of the invention to provide a standby defibrillator which automatically regains sensing control over a functioning hearth, thereby inhibiting further shocks after successful defibrillation.

It is still another object of the invention to provide a device employing a heart-implanted cathether which may sense both for defibrillation and for pacing the heart if required.

It is still another object of the present invention to provide a standby defibrillator which is extremely compact and which is therefor totally implantable in the body of a patient.

These and other objects of the invention, as well as many of the attendant advantages thereof, will become more readily apparent when reference is made to the following description taken in conjunction with the accompanying drawings.

DETAILED DESCRIPTION OF THE INVENTION

Figure 1:
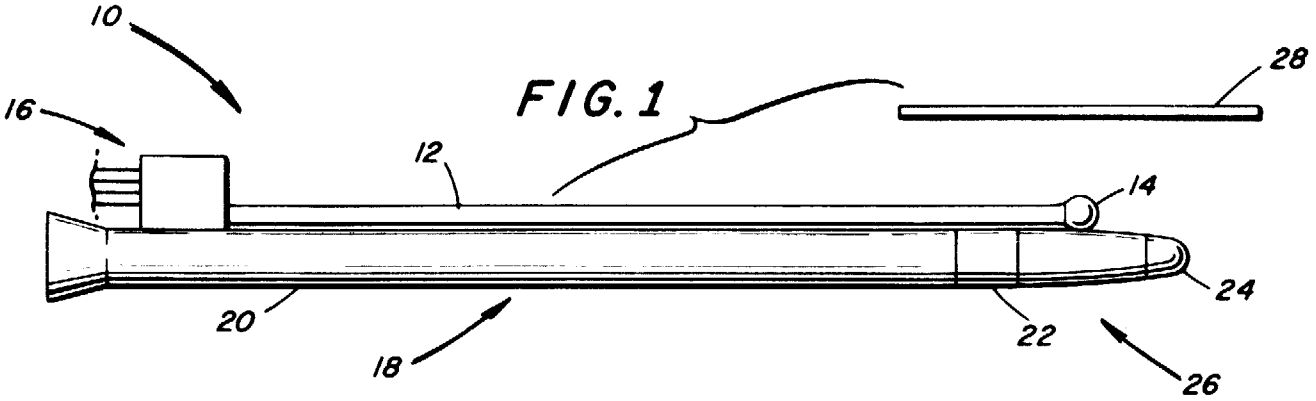
FIG. 1 is a side view of the combination sensing probe and shock-applying probe forming a part of the present invention.

With reference first to FIG. 1, the sensing and shock delivering probes will be described. The sensing probe is shown generally at 10 and comprises a main body portion 12 and a pressure sensitive bulb 14. Electrical connections to the bulb 14 are made at junction box 16. One of the shock delivering probes is shown generally at 18 and comprises a main body portion 20, a first ring electrode 22 and a second ring electrode 24. As will be explained below, the electrodes 22 and 24 are short-circuited together during the operation of the device, forming a composite electrode shown at 26. The main body 12 of the sensing probe 10 is in the shape of a flat ribbon, and the body of the bulb 14 is spherical. The shock delivering probe 18 is substantially cylindrical.

As noted previously, the combination sensing probe 10 and shock delivering probe 18 is, during operation, positioned in the right ventricle of the heart. These probes are introduced into the heart through a peripheral vein by means of surgery very similar to that involved in the implantation of a pacer probe.

The shock delivering electrodes are two in number. The first electrode is the composite electrode 26 and is carried by the shock delivering probe 18. The second electrode is shown at 28 and, in the preferred embodiment of this invention, is a flat plate either placed on the surface of the chest, sutured under the skin of the anterior chest wall or applied directly to the ventricular myocardium.

When the sensing probe 10 and the shock delivering probe 18 are inserted into the heart, the electrodes 22 and 24 are independent of one another. At this time, conventional pacemaking signals are applied between the electrodes 22 and 24. Since the heart responds favorably to the pacemaking signals only if the probe 18 is properly positioned, this method is suitable for checking the position of the probes 10 and 18. The probe location may, of course, be recognized by other methods such as, for example, fluoroscopy or pressure recordings. Once it is determined that the probes 10 and 18 are properly located, they are secured in place and the pacemaking electronics are disconnected. Then, the electrodes 22 and 24 are externally short-circuited together, and the electronic circuit associated with the standby defibrillator of the present invention is then connected to the probes 10 and 18 and the electrode 28. If a pacemaking function is also to be carried out, the pacer electronics will remain connected and the step of shorting together the electrodes 22 and 24 will be eliminated.

Figure 2:
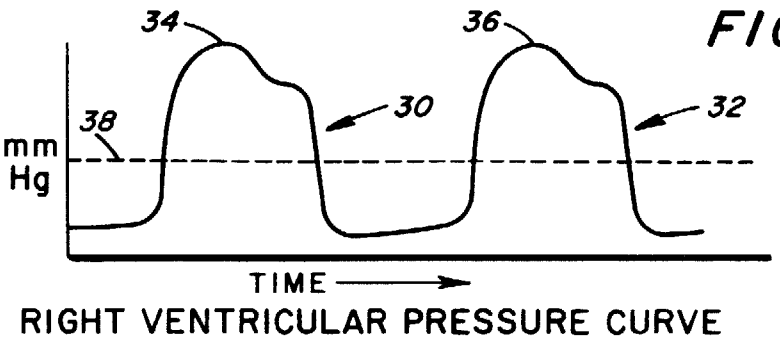
FIG. 2 illustrates a typical pressure curve for the right ventricle of a normally functioning heart.

With reference now to FIG. 2, there is illustrated a right ventricular pressure curve for a normally functioning heart. Pulses 30 and 32 are illustrated but, as is well known, these pulses repeat at the rate of approximately 60 to 70 per minute in a normally functioning heart. FIG. 2 clearly shows that each pulse has a peak and that these peaks rise above a preset pressure indicated by the dotted line 38. This dotted line corresponds to the threshold between a healthy heart and one which is in need of defibrillation. When the height of the peaks 34 and 36 fall below the pressure indicated by line 38, the malfunction is sensed by probe 10 which, as will be described immediately below, initiates the defibrillation of the heart.

Figure 3:
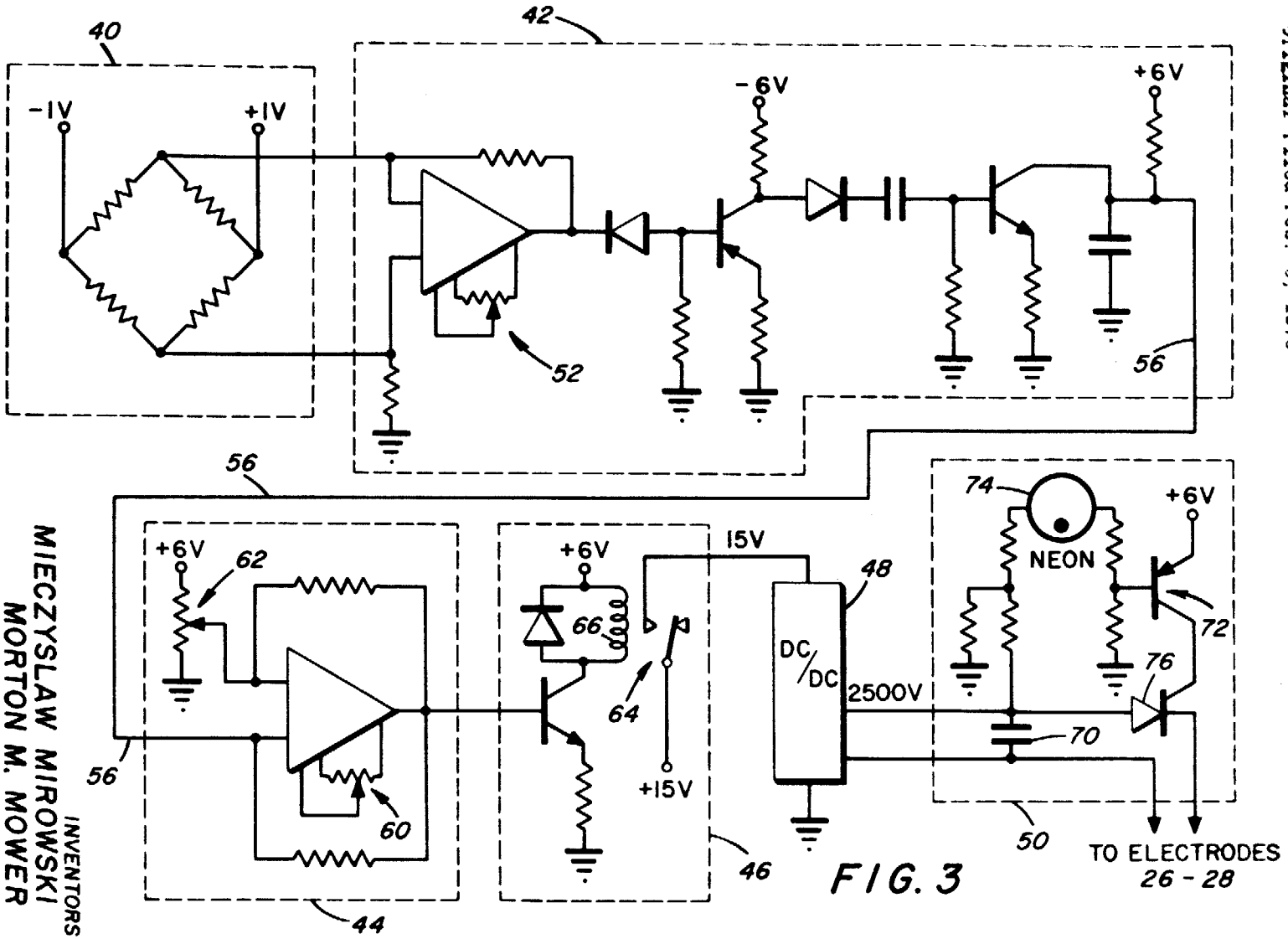
FIG. 3 is a circuit schematic of the electronics comprising the standby defibrillator of the present invention.

With reference then to FIG. 3, the electronics associated with the standby defibrillator will be described. The electronic circuitry of FIG. 3 may conveniently be broken down into several component parts. The first part is a pressure transducer shown at 40, this pressure transducer being directly associated with the pressure sensing probe 10 shown in FIG. 1. The next [state] *stage* of the electronics is [an] *a combination of an* amplifier *and a sawtooth generator* shown at *block* 42. [and] *The amplifier is* adapted to amplify the signals received from the pressure transducer 40. *The sawtooth generator comprises a transistor and a capacitor connected between the cellector electrode of the transistor and ground. The* [amplified] signal from the [amplifier 42] *sawtooth generator* is then passed to [a sawtooth generator] *an output amplifier* shown at 44, which [generator] *amplifier* in turn feeds its output signal to the base of a transistor associated with the relay stage shown at 46. The relay 46 is normally in its open state condition but, when it is closed, a DC signal is impressed upon a DC/DC converter stage 48. The DC/DC converter 48 boosts the input voltage from approximately 15 volts to approximately 2,500 volts. The 2,500 volt DC signal from the converter 48 is then fed to a storage capacitor 70 which is associated with a firing circuit, the entire combination shown at 50. When the firing circuit 50 allows the capacitor 70 to discharge, the 2,500 volt signal is applied to the electrodes 26 and 28 illustrated in FIG. 1. Therefore, when the pressure sensing probe 10 recognizes a malfunction in the heart, the capacitor, after a predetermined time delay, shocks the heart with approximately 2,500 volts. This voltage corresponds to approximately 50 joules of power, enough power to cause most hearts to defibrillate.

Still referring to FIG. 3, but in greater detail, the circuitry associated with the present invention functions as follows. The pressure transducer 40 takes the form of a resistive bridge, one resistor of which is defined by the pressure sensor 14 on the tip of the probe 10. The remaining legs in the bridge are defined by resistors housed in the junction box 16 shown in FIG. 1. The pressure transducer 40 is arranged so that the pressure sensed by element 14 is converted to an electrical signal, the amplitude of which is directly proportional to the pressure sensed by the element 14.

The output from the pressure transducer 40 is fed to a conventional *multistage* amplifier *shown in block* 42 which amplifies the received pulses and which then feeds these amplified pulses to the sawtooth generator *in block 42.* [44.] The trimming potentiometer 52 [seems] *serves* to balance the inputs to the associated amplifier.

Figure 4:
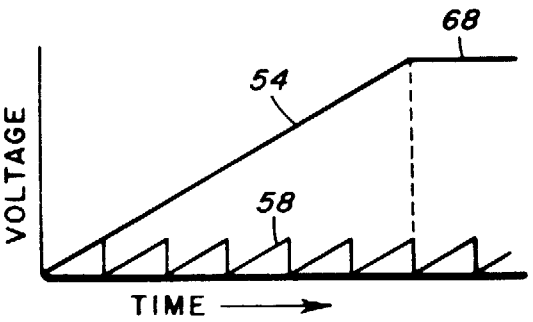
FIG. 4 is a graph of voltage versus time illustrating the operation of the sawtooth generator forming a part of the present invention.

With reference now to FIGS. 2 through 4, the operation of the sawtooth generator [44] will be described. The sawtooth generator [44], if unaffected by the external environment, will have an output curve such as that shown at 54 in FIG. 4. However, if a signal is fed to the sawtooth generator, [via lead 56,] and if the signal is at least of a predetermined amplitude, then the output voltage of the generator *on lead 56* will immediately drop to zero and then again begin to climb. Therefore, if the sawtooth generator receives [repititious] *repetitious* pulses of at least the predetermined voltage, then its output will be similar to that shown in FIG. 4 *by waveform 58.*

If the heart functions sensed by the pressure transducer 40 are normal, following the curve shown in FIG. 2, then the amplified signal corresponding to a pulse in the right ventricular pressure will cause the output of the sawtooth generator [44] to drop to zero. The threshold signal reaching the generator [44 via lead 56], can be adjusted by adjusting the amplification factor of the signal amplifier *shown in block* 42. [This] *Amplifier 44 has a* threshold *which is* adjusted *by potentiometer 62* so that the [generator] *amplifier* 44 activates the relay 64 only after approximately six seconds of heart malfunction. If, then, the ventricular pressure falls lower than that value indicated by the dotted line 38, and so remains for the present time interval, the amplified voltage reaching the generator [44, via lead 56,] will be insufficient to cause the generator output to drop to zero. Rather, the generator output will follow the curve shown at 54 in FIG. 4 *and the threshold of amplifier 44 will be reached.* Trimming potentiometer 60 is provided to balance the inputs *provided* to the associated *output* amplifier *44 from lead 56 and potentiometer 62.*

The output from the [sawthooth generator] *amplifier* 44 is fed to the relay circuit 46. The relay contacts shown generally at 64 are initially set in the open-circuit condition, thereby isolating the 15 volt source from the DC/DC converter 48. Further, the relay 46 is set to close only after the current passing through coil 66 reaches a predetermined value. With reference to FIG. 4, the voltage output of the sawthooth generator [44] must be at the level 68, *the threshold of amplifier 44,* before the current in the coil 66 is sufficient to switch the relay 64 into its closed-circuit state.

When the relay 64 closes, then the 15 volt source is connected directly to the DC/DC converter 48. From FIGS. 2 through 4, it should be evident that approximately six seconds must elapse, with the heart continuously malfunctioning, before the relay 64 switches from its open-circuit mode to its closed-circuit mode. This will be apparent when one realizes that each "tooth" of the curve 58 corresponds to one peak of the right ventricular pressure curve and, as noted above, the peaks of the pressure curve repeat at approximately 60 to 70 per minute. Therefore, the heart pressure must be below the threshold level for approximately six seconds before input voltage is fed to the DC/DC converter 48. If the heart returns to its normal function at any time during that six seconds, then the sawtooth generator output response would drop to zero and the six second cycle would begin again.

With the relay 64 closed and a 15 volt DC signal being impressed upon the converter 48, an output of 2,500 volts appears at the output terminals of the converter 48. This voltage is fed directly to storage capacitor 70. Simultaneously, the 2,500 volt signal is fed to a resistive chain and finally to the base of transistor 72 via a neon tube 74. A silicon controlled rectifier (SCR) is triggered on when transistor 72 becomes conductive.

The operation of the firing circuit 50 is as follows: the 2,500 volt signal from the converter 48 is fed to the capacitor 70. When the capacitor 70 is fully charged, the transistor 72 becomes conductive, due to the now-conducting neon tube 74. The resistor chains and the tube 74 are interconnected in such a manner that when the voltage across the capacitor 70 reaches the full 2,500 volts, then the tube 74 becomes conductive. When the tube 74 conducts, so too does transistor 72 and, therefore, SCR 76. Then, the full 2,500 volts pass through electrodes 26 and 28 thus shocking the heart with a voltage sufficient to cause defibrillation.

As above noted, it is important that a time period elapse between the detection of a heart malfunction and the delivery of the defibrillating shock to the heart. As also noted above, approximately six seconds of delay occur between the first detection of a malfunction and the closing of the relay 64. There is an additional delay, on the order of fifteen seconds, which is brought about by the charge time of the capacitor 70. That is, when the relay 64 closes, six seconds after the initial malfunction, the capacitor first begins to charge. The capacitor employed in the preferred embodiment charges in approximately fifteen seconds. Therefore, approximately twenty-one seconds elapse between the initial sensing of heart malfunction and the discharge of the capacitor into the heart. Naturally by varying the rise time of the sawtooth generator and the charge time of the capacitor, the twenty-one seconds may be enlarged or contracted as desired. And, as mentioned above, if at any time during the delay period the heart returns to normal, then the delay period automatically begins again.

Above, a specific embodiment of the present invention has been described. It should be understood, however, that this description is given for illustrative purposes only and that many alterations and modifications may be practiced without departing from the spirit and scope of the invention. Just as a few examples, it should be understood that while in the specific embodiment of the present invention, the pressure in the right ventricle is sensed as an indication of heart malfunction, other sensing arrangements may be practiced. Further, a single SCR is used as a triggering device. It is possible to substitute this device for a plurality of SCR units or, alternatively, with a vacuum relay. Still further, while the above description shows a single storage capacitor, a series of capacitors could be employed. It is, therefore, the intent that the present invention not be limited to the above but be limited only as defined in the appended claims.

We claim:

1. An electronic device for automatically defibrillating a malfunctioning heart, the device comprising: electronic probe means for continually sensing the function of a heart and for issuing an electrical signal, the amplitude of which is proportional to the heart function; discriminator means associated with said probe means for responding to the electrical signal issued thereby and for issuing an electrical signal of a first amplitude when the heart function is normal and for issuing an electrical signal of a second amplitude when the heart function is abnormal; means for storing electrical energy; electrode means associated with said storage means for connecting the storage means directly to the heart; and means for automatically switching said storage means into a discharge state, in response to the signal of said second amplitude, whereby the stored energy is applied directly to the heart through said electrode means to defibrillate a malfunctioning heart.

2. The device as set forth in claim 1, and further comprising: delay means for ensuring that a time delay exists between the sensing of the initial heart malfunction and the discharge of said storage means into the heart.

3. The device as set forth in claim 1, wherein said sensing means is adapted to be positioned within the heart.

4. The device as recited in claim 1, wherein the means for applying the stored power to the heart comprises two electrodes, one of which is adapted to be positioned within the heart.

5. The device as set forth in claim 2 wherein said switching means includes: means for inhibiting the discharge of said storage means in response to a signal of said first amplitude occurring during said time delay.

6. The device recited in claim 1, wherein said electronic probe includes pressure responsive means which senses the right ventricular pressure and issues an electrical signal whose amplitude is directly proportional to the pressure.

7. The device of claim 1, wherein said discriminator means includes sawtooth generator means having small amplitude output means responsive to normal heart function and large amplitude output means responsive to abnormal heart function, and time delay means connected to the large amplitude output means for delaying large amplitude output for a preset period of time.

8. The device recited in claim 7, wherein said switching means comprises relay means connected to said sawtooth generator means and having normally open contact means adapted to close only when subjected to said large amplitude signal from said discriminator means.

9. The device of claim 8, wherein said means for storing comprises: voltage generator means for generating a voltage sufficient to defibrillate the heart, said voltage generator means operatively connected to said contact means for operating only when said contact means are closed.

10. The device of claim 9 including a capacitor connected directly to the output of said voltage generator means.

11. The device of claim 10, and further comprising: switching means having a normally open-circuit state, said switching means connected to said capacitor for switching to a closed-circuit state after said capacitor has fully charged, the closed-circuit state of said switching means resulting in the discharge of said capacitor into the heart.

12. The device of claim 11, wherein said switching means includes gas lamp means responsive to the charge on said capacitor to operate said switch means.

13. The device of claim 1, wherein said means for automatically switching includes at least one silicon controlled rectifier.

References Cited

The following references, cited by the Examiner, are of record in the patented file of this patent or the original patent.

UNITED STATES PATENTS

| | | | |
|---|---|---|---|
| 3,138,151 | 6/1964 | Chapman et al. | 128—2.05 |
| 3,236,239 | 2/1966 | Berkavits | 128—419 |
| 3,258,690 | 12/1967 | Cohen | 128—419 |
| 3,481,341 | 12/1969 | Siedband | 128—421 |
| 3,144,019 | 8/1964 | Haber | 128—419 P |
| 3,236,239 | 2/1966 | Berkovits | 128—419 D |
| 3,241,556 | 3/1966 | Facouto | 128—419 D |
| 3,585,983 | 6/1971 | Kantrowitz et al. | 128—1 D |
| 3,358,690 | 12/1967 | Cohen | 128—419 P |

FOREIGN PATENTS

| | | |
|---|---|---|
| 1,067,538 | 10/1959 | Germany. |
| 826,766 | 1/1960 | Great Britain. |

OTHER REFERENCES

Frank: German Application No. 1,067,538, Oct. 22, 1959.

Stratbucker et al.: "Rocky Mountain Engineering Society," 1965, pp. 57–61.

WILLIAM E. KAMM, Primary Examiner